(12) United States Patent
Lee

(10) Patent No.: US 11,351,344 B1
(45) Date of Patent: Jun. 7, 2022

(54) EQUINE NASOGASTRIC INTUBATION ADAPTER WITH BACKFLOW DIVERTER

(71) Applicant: Ryan M. Lee, College Station, TX (US)

(72) Inventor: Ryan M. Lee, College Station, TX (US)

(*) Notice: Subject to any disclaimer, the term of this patent is extended or adjusted under 35 U.S.C. 154(b) by 56 days.

(21) Appl. No.: 16/570,479

(22) Filed: Sep. 13, 2019

Related U.S. Application Data

(63) Continuation-in-part of application No. 15/045,232, filed on Feb. 16, 2016, now abandoned.

(60) Provisional application No. 62/117,325, filed on Feb. 17, 2015.

(51) Int. Cl.
*A61M 25/06* (2006.01)
*A61D 7/00* (2006.01)

(52) U.S. Cl.
CPC ........... *A61M 25/0662* (2013.01); *A61D 7/00* (2013.01); *A61M 2205/586* (2013.01); *A61M 2210/0618* (2013.01); *A61M 2210/1053* (2013.01); *A61M 2250/00* (2013.01)

(58) Field of Classification Search
CPC ... A61D 1/14; A61D 1/12; A61D 1/00; A61D 7/00; A61J 15/0003; A61J 15/0026; A61J 15/0096; A61J 15/003; A61M 2210/0618; A61M 2210/1053; A61M 2250/00; A61M 25/0662; A61M 2205/586; A61M 1/00; A61M 1/0023; A61M 2025/0226; A61M 16/0461
See application file for complete search history.

(56) References Cited

U.S. PATENT DOCUMENTS

| | | | | |
|---|---|---|---|---|
| 4,111,204 A | * | 9/1978 | Hessel | A61M 1/604 604/321 |
| 4,764,167 A | * | 8/1988 | Tu | A61M 1/782 604/173 |
| 4,791,914 A | * | 12/1988 | May | A61M 1/0023 600/573 |
| 5,255,687 A | * | 10/1993 | McKenna | A61B 5/097 128/205.24 |
| 5,609,149 A | * | 3/1997 | Takach | A61M 16/0009 128/200.24 |
| 2012/0016337 A1 | * | 1/2012 | Khalaj | A61M 1/0001 604/506 |

* cited by examiner

*Primary Examiner* — Bhisma Mehta
*Assistant Examiner* — Hong-Van N Trinh
(74) *Attorney, Agent, or Firm* — Harrison Law Office, P.C.

(57) ABSTRACT

A rigid hollow tubular adapter releasably attached at a longitudinal nozzle end to a flexible tube during equine nasogastric intubation comprising an annular sleeve having a stationary tubular member and a slidable tubular member. The slidable tubular member is delimited at its ends by the stationary tubular member and a detent member disposed between an equine reflux drainage hole and a longitudinal mouthpiece end. Operator's puffs of airflow through a mouthpiece urges the slidable member to slide toward the detent member closing the equine drainage hole to enable passage of medication into the equine stomach. Equine reflux urges the slidable tubular member to slide toward the stationary tubular member opening the reflux drainage hole to divert equine backflow downwardly through the equine backflow drainage hole preventing passage of equine reflux into the operator's mouth.

9 Claims, 6 Drawing Sheets

EQUINE NASOGASTRIC INTUBATION ADAPTER WITH BACKFLOW DIVERTER

RELATED APPLICATIONS

This application is a continuation-in-part of pending U.S. application Ser. No. 15/045,232 filed Feb. 16, 2016.

FIELD OF THE INVENTION

The present invention generally relates to nasogastric intubation, and more particularly relates to an apparatus enabling an operator, typically a veterinarian or other medical professional, to safely conduct equine nasogastric intubation without jeopardizing the horse's well-being and simultaneously avoiding ingestion or aspiration of contaminated air emanating from equine breath while coughing and also of contaminated liquid emanating from the equine stomach into the operator's mouth while nasogastric intubation is being conducted.

BACKGROUND OF THE INVENTION

As is well known by veterinarians specializing in equine practice, a horse is a non-ruminant herbivore having a digestive system configured with unique anatomical attributes. For instance, a horse has a large gastrointestinal tract about one hundred feet long, primarily consisting of the small and large intestines. The small intestine interconnects the stomach with the large intestine, through its two inch diameter and constitutes about 30% of the equine digestive tract. It is typically fifty to seventy feet long having a capacity of about ten to fifteen gallons. Most food is digested and absorbed into the bloodstream in the small intestine, with any residual roughage and liquids being transferred to the large intestine.

The equine large intestine is typically fifteen to twenty feet long having a diameter as small as two to three inches in one portion, to eight to ten inches in another portion, and as large as about twenty inches in another, lower abdominal portion thereof. Thus, the equine large intestine has diameters throughout that are significantly larger than the diameter of the small intestine—with a capacity of more than thirty gallons. Bacteria residing therein enable digestion of cellulose plant fiber via fermentation, wherein plant fiber is broken down into carbohydrates which may then be readily absorbed in the large intestine. A horse has a relatively small, single-compartment stomach typically having a capacity of about 4 gallons, corresponding to about ten percent of the digestive system. Unlike other species, the oral spinchter of the equine stomach is very tight and doesn't allow retrograde movement of any material. Accordingly, horses are unable to vomit or eructate gas.

Digestion commences in the oral cavity when a horse ingests plant food. The ingested food is masticated in the mouth and then transported to the stomach through an elongated esophagus tube, typically four to five feet long, urged by peristaltic wave-like contractions that are propagated by a well-developed muscular ring interconnecting the esophagus therewith.

It is also well known by practitioners in the art that colic, manifest as abdominal pain, is a common equine emergency attributable to such circumstances as attenuated movement of the small intestine and/or obstructions therein; inhibited movement of the large intestine and/or obstructions therein and/or twisting or displacement thereof. The result of these phenomena could include accumulation of fluid in the horse's stomach. A known factor causing such problematic accumulation is a horse being unable to eructate. The equine cardiac spinchter is so tight wherein passage of gas, liquid or other material retrograde is disallowed. Thus, it will be appreciated that there are several underlying causes for colic which, of course, range from mild and inconsequential to severe and life-threatening. Accordingly, in the abundance of caution, every occurrences of colic should preferably be handled with urgency, as the equine stomach or intestine can rupture due to backup pressures during gastrointestinal disfunction.

Nasogastric intubation is routinely invoked by veterinarians to treat equine medical conditions such as colic and chokes, or to gain access to the stomach for evaluation or to deliver medication. In its most common application, nasogastric intubation is used during colic treatment to facilitate decompression of the stomach and to administer therapy. For equine chokes, nasogastric intubation is used to clear occlusions of the esophagus. It should be understood that such obstructions must be promptly remedied to avoid feed and fluid being urged to pass into an occluded oropharynx forcing these materials toward the lungs as a horse attempts to swallow. As is known in the art, notwithstanding advent of paste dewormers to clear occlusions in the esophagus, parasiticides are still routinely administered by invoking a nasogastric tube (herein abbreviated "NGT") to expedite direct access to the troubled equine stomach. And, finally, practitioners in the art will also readily recognize that a NGT is also especially useful for enabling gastric endoscopy to apprise a medical professional of the integrity and condition of equine stomach walls and contents therein.

Once a NGT is emplaced into the ventral nasal passage and into the equine oropharynx the stimulus initiates swallow reflex forcing the NGT into the esophagus. Then a veterinarian can blow small puffs of air thereinto as the NGT is passed into an equine esophagus simultaneously facilitating the NGT's passage. This intermittent blowing via the NGT tends to facilitate dilation of an otherwise collapsed equine esophagus, thereby allowing contemplated aboral movement and subsequent insertion of the NGT into the equine stomach. It will be appreciated by those conversant in the art that the NGT would be advanced until essentially being situated level with the equine twelfth rib.

Upon entry into the equine esophagus, after orally effectuating prerequisite vacuum by imparting a modicum of suction into the NGT, a veterinarian can confirm the NGT has been emplaced properly in the equine esophagus rather than the equine trachea if and when the veterinarian hears gas and/or smells quine stomach contents. It should be appreciated that there would be an absence of negative pressure generated from this modicum of suction if the NGT were incorrectly emplaced into the trachea. Without this functionality, a veterinarian would be left to ausculting of gas or smelling of gastric contents which may or may not be heard or indeed be present. It should be appreciated by those conversant in the art that absent the backflow preventive apparatus functioning as a check valve as herein disclosed, stimulating or tickling the equine pharynx frequently results in aspiration of equine stomach contents into a veterinarian's lungs, and, without the benefit of invoking a backflow preventive apparatus functioning as a check-valve, in view of there being a formidable probability of spontaneous equine reflux occurring, there would typically be a vulnerability that a veterinarian seemingly would unavoidably be exposed to pungent, fermented or even bloody reflux constituting a health hazard and/or a biohazard thereto.

The prior art appears to be devoid of any convenient and sufficiently portable apparatus that reliably enables a veterinarian or other medical professional to safely engage in equine nasogastric intubation as contemplated herein.

SUMMARY OF THE INVENTION

The present invention contemplates an equine nasogastric intubation adapter structured to allow an operator, typically a veterinarian or other medical professional, to manually administer suction or puffs of air while simultaneously preventing or diverting equine stomach reflux from entering the operator's mouth. More particularly, embodiments of the present invention facilitate an operator effectuating safe passage of a NGT upwardly through the equine ventral nares into the nasopharynx and pharynx, wherein the horse is induced to swallow urging the NGT into the equine esophagus.

It will be readily understood that the equine esophagus is typically collapsed in its resting state. So, prior to conducting nasogastric intubation, an operator must cause this esophagus to be expanded to permit and accommodate NGT-passage therethrough. Hence, the operator would preferably blow gently through the NGT to apply minimal pressure to urge the equine esophagus to expand.

Embodiments of the instant equine nasogastric longitudinal intubation adapter would be configured to be easily and conveniently be attached at a male end of a variety of suitably sized flexible tubes or flexible hoses. It will be seen that such embodiments comprise a rigid hollow tubular member having an annular sleeve member contained axially therein. The annular longitudinal sleeve member comprises a first stationary member configured to be affixed to one end of the tubular adapter and a slidable tubular member configured to be slidably displaced from being disposed adjacent the stationary tubular member to being disposed remotely thereof as will be hereinafter described. Thus, the slidable tubular member is readily urged to slide within the annular sleeve member from a first position adjacent the stationary tubular member to a second position remote of the stationary tubular member toward the opposite end of the tubular adapter until abutting and adjacent a detent member. It will be evident to those skilled in the art that each of these two delimiting positions are disposed on opposite sides of an equine reflux drainage hole which is, in turn, disposed between the stationary tubular member and the detent member.

The proximal end of the nasogastric intubation adapter has a mouthpiece emplaced within the operator's mouth simultaneously with the other distal, opposite end thereof having a nozzle member preferably circumscribed by a series of undulating diminishing diameters or ridges conveniently and securely releasably attached to a flexible tube or flexible hose sized to comfortably and safely be inserted into the equine digestive system through the equine nasal cavity. Preferred embodiments comprise a mouthpiece having a pair of bite-tabs with a pliable plastic shield enabling hands-free gripping and, more particularly, teeth-gripping thereof at the proximal end to sustain its uninterrupted presence in the operator's mouth while appropriate treatment is being administered.

It is an object and advantage of the present invention to serve as a safety interface while providing a convenient, inexpensive and lightweight portable adapter that attaches to a flexible tube or flexible hose incorporated into an equine nasogastric intubation protocol.

It another object of the present invention to provide a disposable equine nasogastric intubation backflow diverter adapter tube that minimizes risk to an operator attributable to equine contamination and concomitant biohazards.

It yet another object of the present invention to provide a disposable equine nasogastric intubation backflow diverter adapter tube that enables safe and convenient emplacement of a nasogastric tube into an equine stomach.

These and other objects and advantages of the present invention will become apparent from the following specification and accompanying drawings.

DETAILED DESCRIPTION

Figure 1:
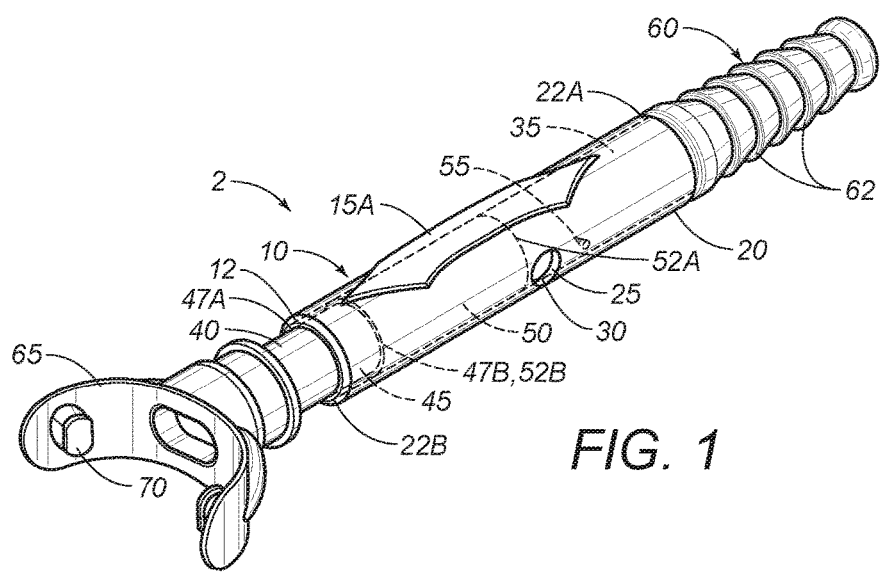
FIG. 1 depicts a perspective side view from the mouthpiece end of an embodiment of the present invention, with the backflow drainage hole disposed in an open position.
Figure 2:
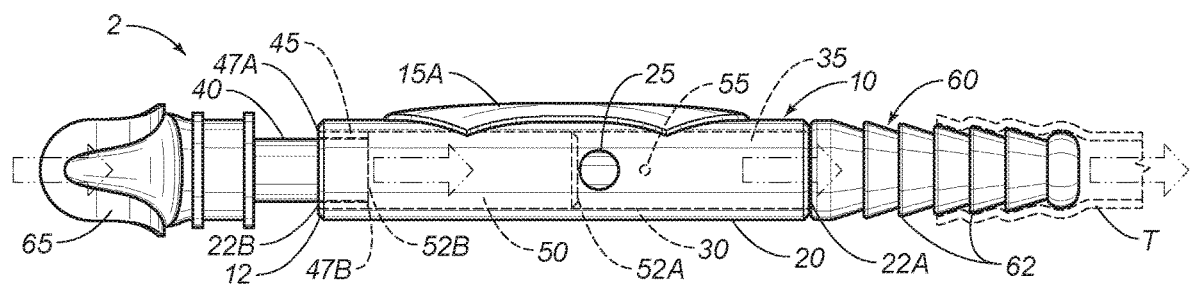
FIG. 2 depicts a side view of an embodiment of the present invention, with the backflow drainage hole disposed in an open position.
Figure 9:
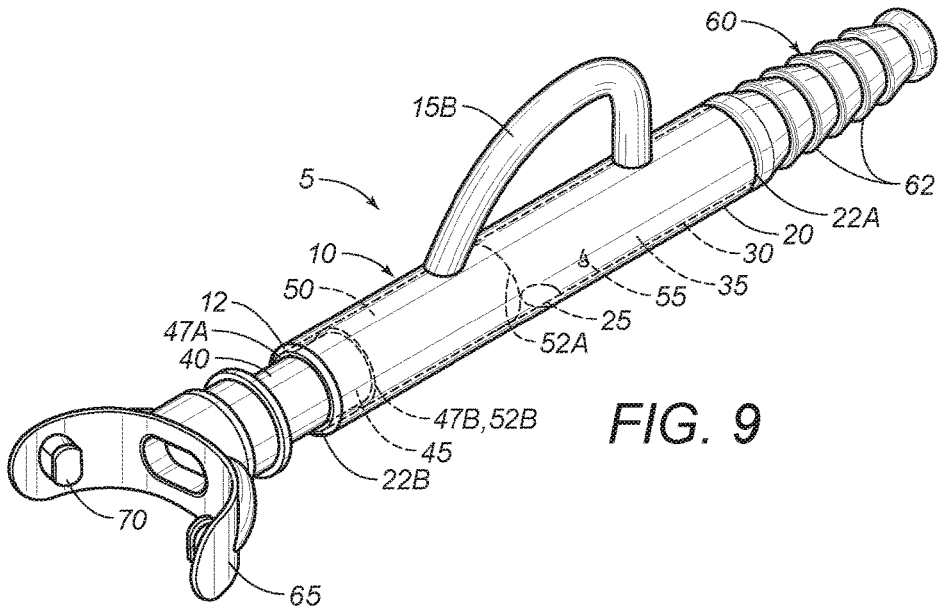
FIG. 9 depicts a perspective side view from the mouthpiece end of another embodiment of the present invention, with the backflow hole disposed in an open position.
Figure 10:
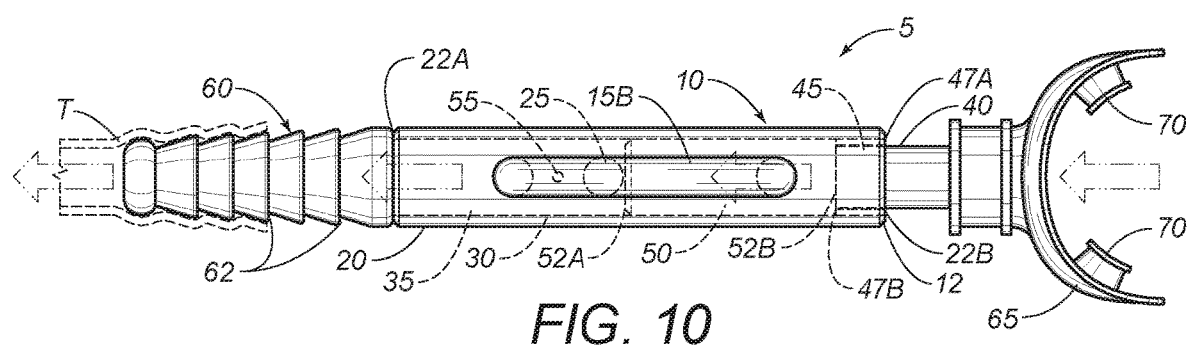
FIG. 10 depicts a top view of the embodiment depicted in FIG. 9.

Reference is made herein to the figures in the accompanying drawings in which like numerals refer to like components. Referring collectively to FIGS. 1-5, 6A-6B, 7-13, 14A-14B, and 5-16, there are depicted various views of two alternative embodiments of the present invention. One embodiment of equine nasogastric intubation backflow diverter adapter 2 is depicted in perspective view in FIG. 1 and another backflow diverter adapter embodiment 5 is depicted in perspective view in FIG. 9.

More particularly, referring collectively to FIGS. 1-5, 6A-6B, and 7-8, there is depicted equine nasogastric hollow tubular backflow preventer adapter embodiment 2 having substantially flat grip member 15A fixedly disposed atop exterior surface 20 of rigid hollow tubular member 10, and disposed axially and centrally therewithin as shown. Exterior surface 20 is preferably configured with beveled or chamfered edge 12 to enhance interconnection with a mouthpiece member 65 disposed at end 22B of rigid hollow tubular member 10 as will be hereinafter described. Annular tubular sleeve member 40 having a circular cross-section is disposed longitudinally upon interior surface 30 of rigid hollow tubular member 10. Bore 35 is circumscribed by interior surface 30 and disposed both axially and centrally therethrough.

Disposed oppositely of end 22B, end 22A of rigid hollow tubular member 10 is configured with nozzle member 60 preferably circumscribed by series of undulating diminishing diameters or ridges 62 as the nozzle remote end is approached. Thus, nozzle member 60 is configured to be releasably and securably attached to a flexible tube or flexible hose T sized to be comfortably and safely inserted into an equine digestive system through an equine nasal cavity (not shown). It will be appreciated that end 22B of rigid hollow tubular member 10 is preferably configured with snorkel-like mouthpiece 65 having pair of bite-tabs 70 with a pliable plastic shield enabling an operator's hands-free, mouth-teeth-gripping thereof at the proximal end to sustain its uninterrupted presence in the mouth of an operator administering the nasogastric procedure contemplated hereunder.

Still focusing on FIGS. 1-5, 6A-B, and 7-8, there are seen different views of the backflow diverter aspect contemplated by the present invention. Thus, annular tubular sleeve member 40 disposed axially and centrally within rigid hollow tubular member 10 comprises a first, stationary tubular member 45 and a second, slidable tubular member 50, configured to be disposed adjacent each other and preferably being congruent, having substantially the same diameter and material of construction.

Stationary member 45 and slidable member 50 are disposed in an adjacent relationship, when there is equine stomach backflow or when the horse coughs thereby instigating movement from nozzle end 22A toward mouthpiece end 22B, in turn, urging slidable member 50 to slide toward stationary member 45 wherein end 47B of stationary member 45 abuts proximal end 52B of slidable member 50. Thus, under this equine backflow condition, positioning of slidable tubular member 50 within axial bore 35 is delimited by corresponding end member 47B of stationary tubular member 45 and end member 52B of slidable tubular member 50, respectively, wherein backflow drainage hole 25 is disposed in an open position (See FIGS. 1-2).

Contrariwise, to commence the nasogastric intubation procedure contemplated hereunder, an operator would impart air flow through mouthpiece end 22B of rigid hollow tubular member 10 by gently blowing into the mouthpiece 65 causing the equine esophagus to expand. It will be appreciated that this gentle airflow travels around sliding member 50 thereby urging it to slide toward and cease movement at detent 55 thereby completely covering equine drainage hole 25 (see FIG. 4) enabling uninterrupted, continuous flow of medication or the like into the equine stomach as intended. Once proper placement of NGT T has been accomplished, embodiments 10 of the instant equine nasogastric intubation adapter would be removed.

Those skilled in the art will appreciate that equine backflow would engender greater momentum than gentle blows of an operator's breath so that positioning of slidable member 50 would be urged to slidably move from being emplaced adjacent detent member 55 at end member 22A of rigid hollow tubular member 10 to being emplaced adjacent end member 47B of stationary member 45 at end member 22B of rigid hollow tubular member 10, assuring opening of equine reflux backflow hole 25.

It will be understood that operator-generated gentle airflow through mouthpiece 65 urges separation of slidable member 50 from stationary tubular member 45 through rigid hollow tubular member 10 until positioning of slidable member 50 within bore 35 is delimited by detent member 55. Accordingly, slidable member 50 abuts detent member 55 at edge 52A thereof, assuring closure of reflux backflow drainage hole 25 (See FIGS. 4-5).

Figure 3:
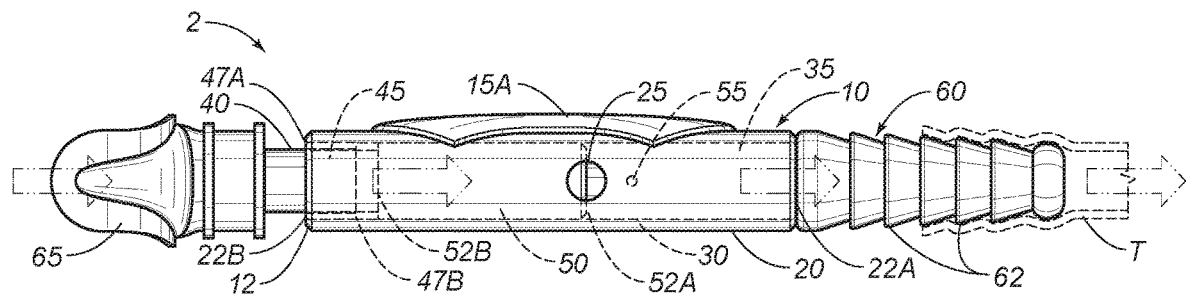
FIG. 3 depicts a side view of the embodiment depicted in FIG. 1, with the backflow drainage hole disposed in a partially-open position.
Figure 4:
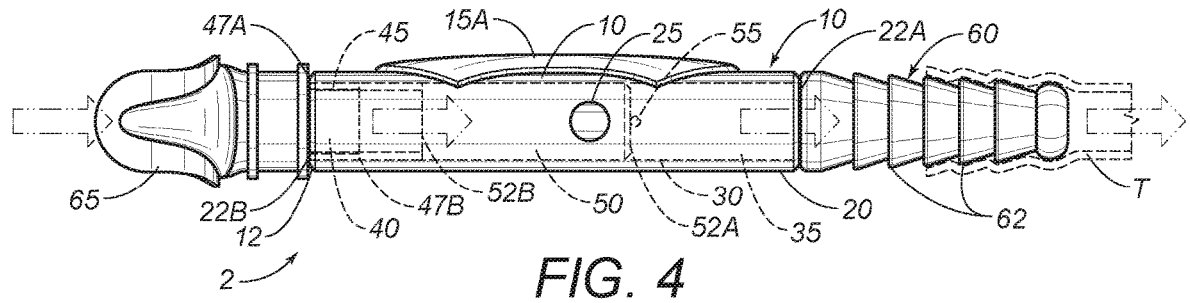
FIG. 4 depicts a side view of the embodiment depicted in FIG. 1, with the backflow hole disposed in a closed position.
Figure 5:
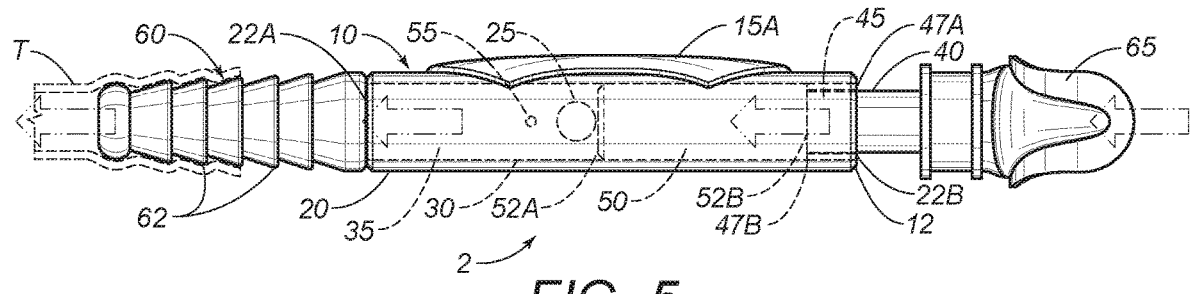
FIG. 5 depicts an opposite side view of the embodiment depicted in FIG. 4.
Figure 6A:
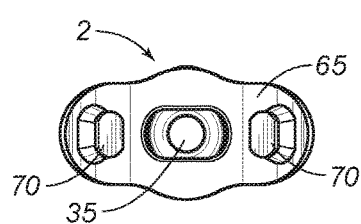
FIG. 6A depicts an end view of the embodiment depicted in FIG. 1.
Figure 6B:
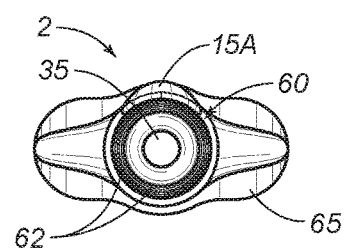
FIG. 6B depicts the opposite end view of the end view depicted in FIG. 6A.
Figure 7:
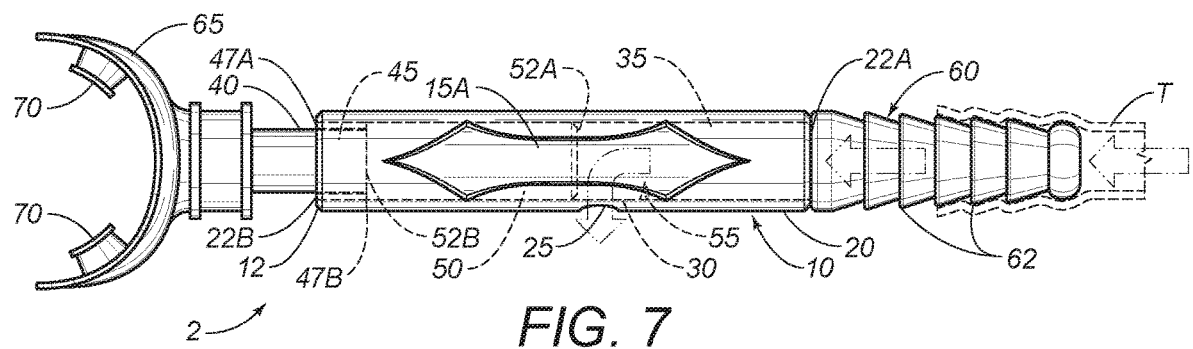
FIG. 7 depicts a top view of the embodiment depicted in FIG. 1.
Figure 8:
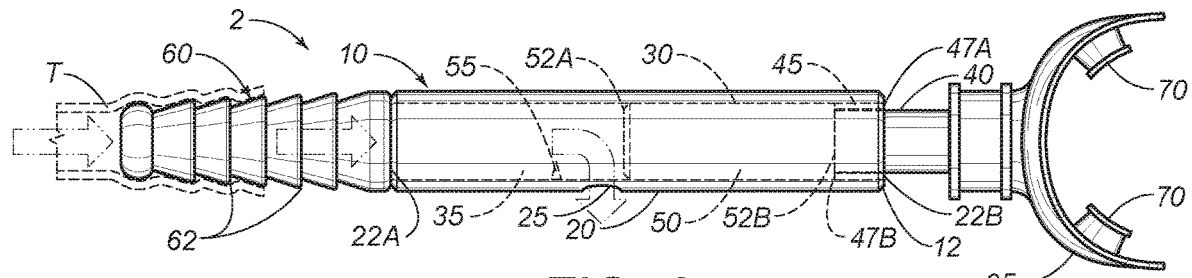
FIG. 8 depicts a bottom view of the embodiment depicted in FIG. 1.

It will also be understood by those skilled in the art, that, as depicted in FIG. 3, the position of slidable member 50 within bore 35 has been slidably urged by equine backflow to the extent of only being partially moved toward detent member 55, wherein equine reflux backflow drainage hole 25 is emplaced essentially in a "half-open" position. It will be seen that detent member 55 and stationary member 45 are disposed on opposite sides of backflow drainage hole 25, wherein detent member 55 comprises a firm nipple member affixed to and protruding minimally from interior surface 30 of rigid hollow tubular member 10. To afford sufficient detent capability for effectively stopping further sliding progress of slidable tubular member 50, the nipple member should be constructed from solid material to be firm enough to cease movement of slidable tubular member 50 toward the longitudinal nozzle end of rigid hollow tubular member 40 as contemplated hereunder wherein equine drainage hole 25 would be completely covered. For instance, such nipple member could constitute a simple cut-off nail-head or similar cut-off screw-top affording sufficient height differential above interior surface 30 to prevent further sliding movement of slidable tubular member 50—beyond this prescribed sliding-movement-limiting position as depicted herein.

As will become evident to those skilled in the art, the present invention contemplates that equine backflow drainage hole 25 will be open when equine liquid reflux or like effluent effectuates backflow pressure in NGT T attached to end 22A of adapter 2 to urge slidable member 50 to slide from emplaced adjacent detent member 55 toward opposite end 22B of rigid hollow tubular member 10 of adapter 2 to another position adjacent stationary member 45. When common end 52B of slidable member 50 is emplaced adjacent of and delimited by common end 47B of stationary member 45, its exterior surface 20 is clear of backflow drainage hole 25, thereby enabling backflow drainage hole 25 to be disposed in an open position enabling equine backflow to be diverted downwardly through equine backflow drainage hole 25 wherein equine backflow is inherently prevented from entering an operator's mouth.

Mouthpiece member 65 is releasably attached to end 22B, disposed oppositely of end 22A of rigid hollow tubular member 10, to enable adapter embodiments hereof to be securely inserted into an operator's mouth and sustained therein hands-free during the equine nasogastric intubation procedure. In this arrangement, as elucidated hereunder, equine reflux is diverted from remaining in the main path from the equine stomach into the operator's mouth, and, instead, urged to flow into a fail-safe diverted downward path through drainage hole 25 into a reflux collection pail or an otherwise designated repository such as the ground (not shown).

It will also be appreciated by those conversant in the art that another embodiment of the present invention could be similarly configured with a single diameter tubular member and with a loop handle member rather than a flat grip member. More particularly, FIGS. 9-13, 14A-14B, and 15-16 depict another embodiment of equine NGT backflow preventer adapter 5 having loop grip member 15B fixedly disposed atop external surface 20 of rigid hollow tube member 10. External surface 20 is preferably configured with beveled or chamfered edge 12. Annular sleeve 40 having circular cross-section is disposed upon interior surface 30 of rigid hollow tubular member 10 as has been hereinbefore described. Bore 35 is circumscribed by interior surface 30 and both axially and centrally disposed therethrough.

Figure 11:
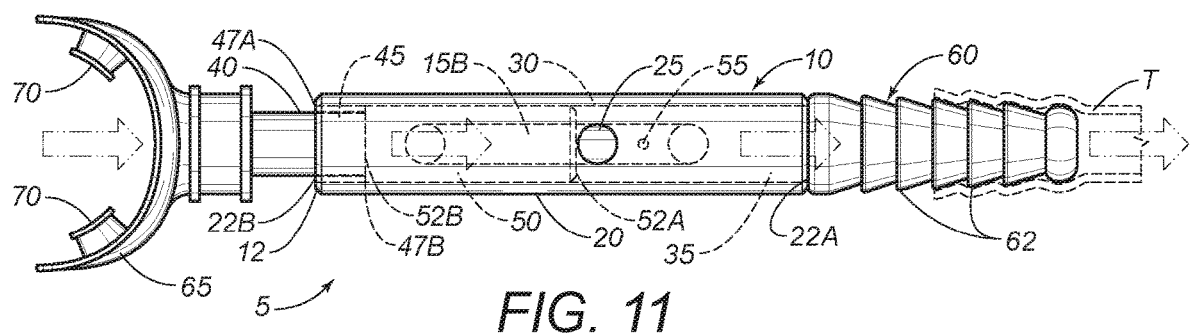
FIG. 11 depicts a bottom view of the embodiment depicted in FIG. 9, with the backflow hole disposed in an open position.
Figure 12:
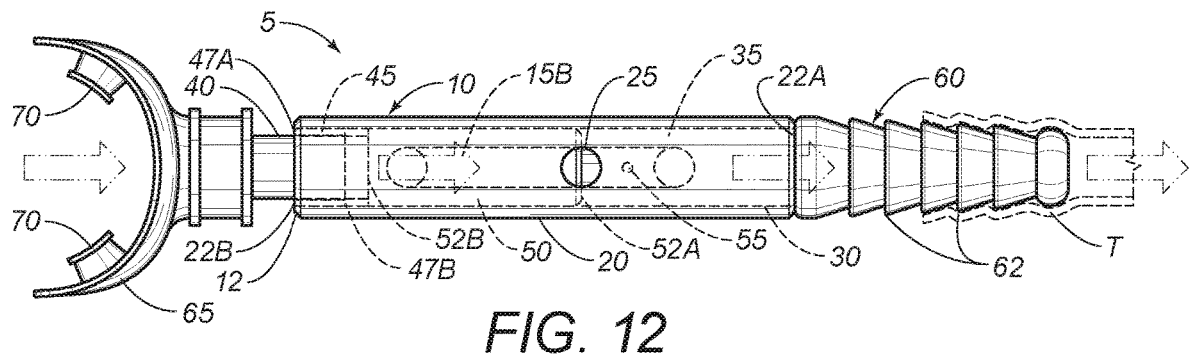
FIG. 12 depicts a bottom view of the embodiment depicted in FIG. 9, with the backflow hole disposed in a partially-open position.
Figure 13:
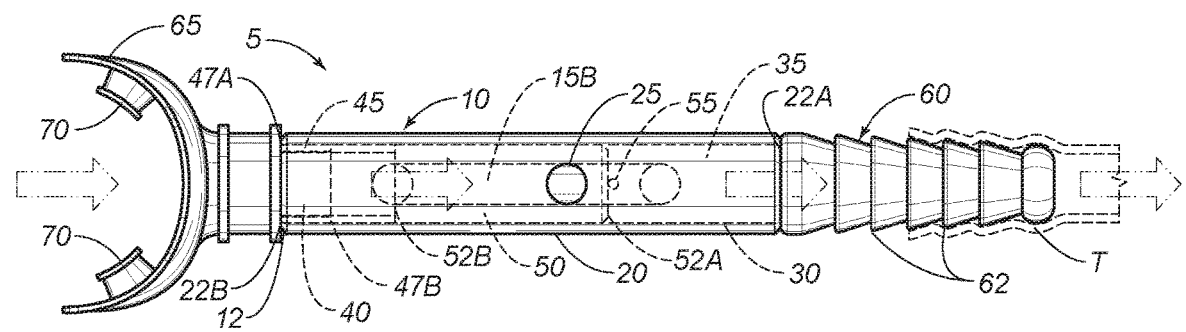
FIG. 13 depicts a bottom view of the embodiment depicted in FIG. 9, with the backflow hole disposed in a closed position.
Figure 14A:
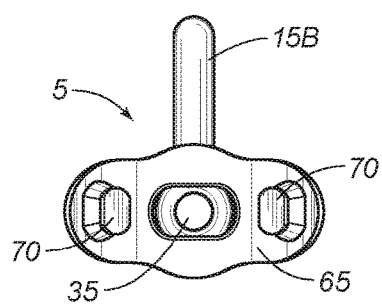
FIG. 14A depicts an end view of the embodiment depicted in FIG. 9.
Figure 14B:
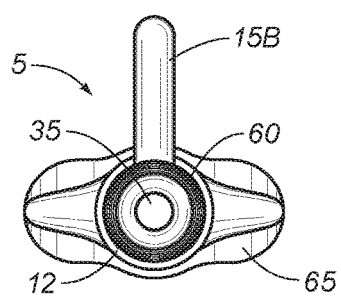
FIG. 14B depicts the opposite end view of the end view depicted in FIG. 14A.
Figure 15:
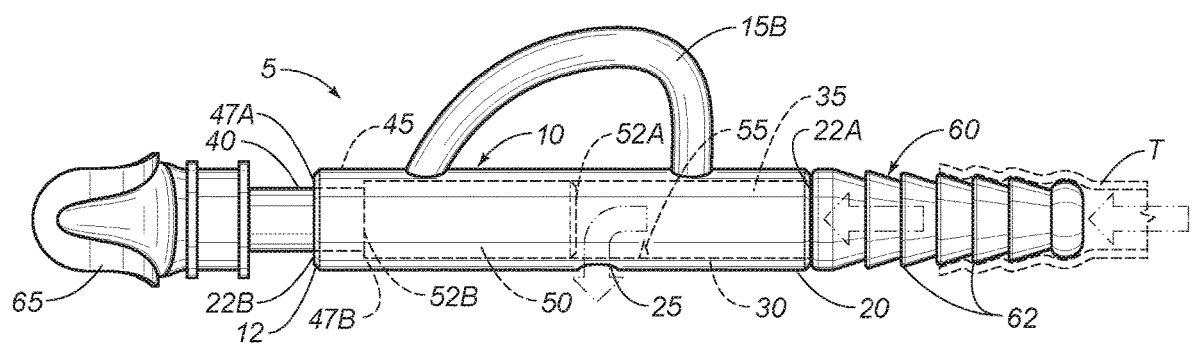
FIG. 15 depicts a side view of the embodiment depicted in FIG. 9.
Figure 16:
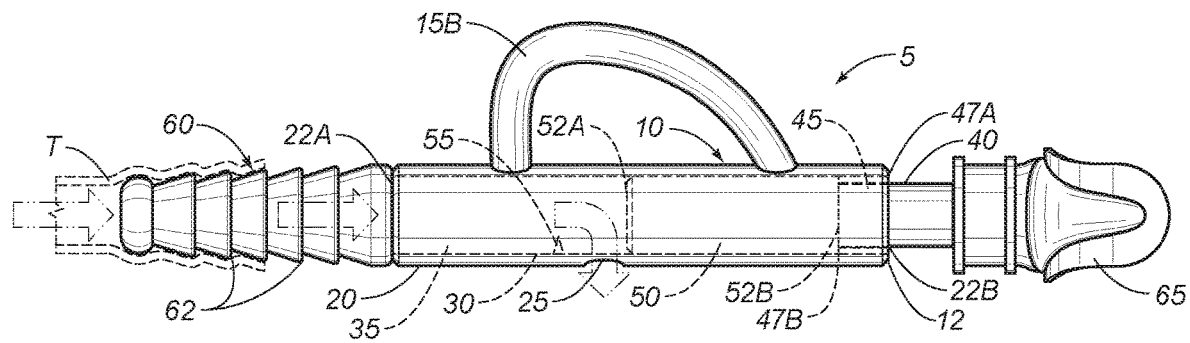
FIG. 16 depicts the opposite side view of the embodiment depicted in FIG. 15.

Focusing collectively on FIGS. 9-13, 14A-B, and 15-16, there are seen different views of the backflow diverter aspect taught by embodiments of the present invention. Thus, interior surface 30 fixedly receives stationary member 45 and slidable member 50, configured to be disposed adjacent each other and preferably congruent and having the same material of construction. When disposed in an adjacent relationship as depicted in FIG. 11, positioning of slidable member 50 within bore 35 is delimited by corresponding common end 47B of stationary member 45 and common end 52B of slidable member 50, respectively, wherein reflux backflow drainage hole 25 is disposed in an open position. Contrariwise, when slidable member 50 is slidably separated from stationary member 45, as depicted in FIGS. 12 and 13, positioning of slidable member 50 within bore 35 is delimited by detent member 55, wherein backflow drainage hole 25 is disposed in a closed position. Referring again collectively to FIGS. 8-14, it will be seen that detent member 55 and stationary member 45 are disposed on opposite sides of equine backflow drainage hole 25 (see end 47B of stationary member 45 and detent member 55 disposed oppositely of drainage hole 25).

The following is a tabulation of the components depicted in the drawings:

Component Listing

| Numeral | Component | Explanation |
| --- | --- | --- |
| 2 | Equine nasogastric tube backflow diverter adapter | Flat grip embodiment |
| 5 | Equine nasogastric tube backflow diverter adapter | Loop grip embodiment |
| 10 | Rigid Hollow Tubular Member | |
| 12 | Beveled or chamfered edge | |
| 15A | Flat grip | Rubberized |
| 15B | Loop grip | |
| 20 | Exterior surface | |
| 22A, B | Respective ends of Rigid Hollow Tubular Member | 22A: nozzle end 22B: mouthpiece end |
| 25 | Backflow Drainage Hole, | Lateral |
| 30 | Interior surface | |
| 35 | Axial bore | |
| 40 | Annular sleeve | |
| 45 | Stationary member | |
| 47A, B | Respective ends of Stationary member | End 47B receives end 52B of slidable member 50 |
| 50 | Slidable member | |
| 52A, B | Respective ends of Slidable Member | End 52B receives end 47B of stationary member 45 |
| 55 | Detent member | Limiting movement of slidable member; nipple-like structure attached to and protruding minimally from interior surface |
| 60 | Nozzle member | Receiving NGT |
| 62 | Series of diminishing diameters or ridges, diminishing as remote, open end of nozzle is approached | Facilitate secure interconnection of flexible tube or hose with adapter |
| 65 | Mouthpiece member | Disposed oppositely of nozzle |
| 70 | Bite-Tab member | Conveniently hold adapter hands-free |

Other variations and modifications will, of course, become apparent from a consideration of the structures and techniques hereinbefore described and depicted. Accordingly, it should be clearly understood that the present invention is not intended to be limited by the particular features and structures hereinbefore described and depicted in the accompanying drawings, but that the present invention is to be measured by the scope of the appended claims.

What is claimed is:

1. A portable equine nasogastric intubation adapter comprising:
a rigid hollow tubular member having a first longitudinal end and having a nozzle member disposed axially of said first longitudinal end for releasably being attached to a flexible tube or a flexible hose by an operator, while said operator positions said rigid hollow tubular member using a grip member fixedly attached to an exterior surface of said rigid hollow tubular member and disposed between said first longitudinal end and an opposite second longitudinal end of said rigid hollow tubular member;
an annular sleeve member disposed axially within said rigid hollow tubular member and circumscribing an axial centrally disposed bore;
said annular sleeve member comprising a stationary tubular member affixed at said first longitudinal end of said rigid hollow tubular member; and a slidable tubular member slidably disposed upon said rigid hollow tubular member;
an equine reflux drainage hole disposed upon an interior surface of said rigid hollow tubular member and further disposed between said first longitudinal end and said opposite second longitudinal end of said rigid hollow tubular member; and
said slidable tubular member urged to slidably move upon said rigid hollow tubular member between a first position adjacent said stationary tubular member and a second position toward said first longitudinal end of said rigid hollow tubular member abutting a detent member affixed upon and protruding upwardly from said interior surface of said rigid hollow tubular member and disposed between said equine reflux drainage hole and said first longitudinal end of said rigid hollow tubular member.

2. The portable equine nasogastric intubation adapter recited in claim 1, wherein said detent member comprises a firm nipple member.

3. The portable equine nasogastric intubation adapter recited in claim 1, wherein said nozzle member comprises a series of undulating diminishing diameters or ridges circumferentially emplaced upon said nozzle member for conveniently and securably releasably attaching said flexible tube or flexible hose sized to be comfortably and safely inserted into an equine nasal cavity and passed therethrough to an equine esophagus and into an equine stomach.

4. The portable equine nasogastric intubation adapter recited in claim 3, wherein said opposite second longitudinal end of said rigid hollow tubular member is configured with a snorkel-like mouthpiece member having a pair of bite-tabs with a pliable, plastic shield disposed on each side of said mouthpiece member enabling said operator's hands-free, mouth-teeth gripping of said portable equine nasogastric intubation adapter while being inserted into said equine stomach through said equine nasal cavity.

5. The portable equine nasogastric intubation adapter recited in claim 4, wherein said equine reflux drainage hole is disposed in a closed position when said slidable tubular member is urged by gentle puffs of breath emanating from said operator's mouth into said mouthpiece member and through said rigid hollow tubular member to be slidably positioned toward and adjacent said detent member thereby covering said equine reflux drainage hole to enable passage of medication into said equine stomach.

6. The portable equine nasogastric intubation adapter recited in claim 5, wherein said equine reflux drainage hole is disposed in an open position when said slidable tubular member is urged by backflow of equine reflux entering into said rigid hollow tubular member through said nozzle member disposed at said first longitudinal end of said rigid hollow tubular member to slide away from said detent member toward said stationary tubular member until positioned adjacent thereto at said opposite second longitudinal end of said rigid hollow tubular member, thereby uncovering said equine reflux drainage hole to divert passage of said equine reflux downwardly through said equine reflux drainage hole and simultaneously disable passage of said equine reflux into said operator's mouth.

7. The portable equine nasogastric intubation adapter recited in claim 1, wherein said grip member comprises a substantially flat member.

8. The portable equine nasogastric intubation adapter recited in claim 1, wherein said grip member comprises a loop member.

9. The portable equine nasogastric intubation adapter recited in claim 1, wherein end members of said rigid hollow tubular member each comprises a bevel member.

\* \* \* \* \*